United States Patent [19]
Phillips

[11] Patent Number: 5,848,975
[45] Date of Patent: Dec. 15, 1998

[54] BREATH TEST FOR *HELICOBACTER PYLORI*

[75] Inventor: Michael Phillips, For Lee, N.J.

[73] Assignee: St. Vincent's Medical Center of Richmond, Staten Island, N.Y.

[21] Appl. No.: 939,861

[22] Filed: Sep. 29, 1997

Related U.S. Application Data

[63] Continuation of Ser. No. 674,249, Jul. 1, 1996, abandoned.

[51] Int. Cl.⁶ ........................................................ A61B 5/08
[52] U.S. Cl. ......................... 600/532; 600/300; 600/543; 128/898
[58] Field of Search ............................ 128/898; 600/529, 600/532, 300, 543; 422/84, 85

[56] References Cited

U.S. PATENT DOCUMENTS

| 4,830,010 | 5/1989 | Marshall | 128/630 |
| 4,947,861 | 8/1990 | Hamilton | 128/719 |
| 5,719,052 | 2/1998 | Ito et al. | 435/287.1 |

FOREIGN PATENT DOCUMENTS

| 8909078 | 10/1989 | WIPO | 422/85 |

*Primary Examiner*—John P. Lacyk
*Assistant Examiner*—Rosiland Kearney
*Attorney, Agent, or Firm*—Kane, Dalsimer, Sullivan, Kurucz, Levy, Eisele and Richard

[57] ABSTRACT

To optimize the $^{14}$C-urea breath test for *Helicobacter pylori* (a) a collection method for alveolar breath samples, (b) varying the post-dosage breath collection time and (c) varying the concentrations of KOH in the liquid trap employed for the capture of $^{14}CO_2$ are employed. Collection of alveolar breath samples in bags was convenient for user and patient. The test provided optimal sensitivity and specificity for the detection of *H. pylori* infection when breath collections were performed 10 min after dosage with $^{14}$C-urea, and when breath $CO_2$ was captured in liquid traps containing 80 or 800 mM KOH.

1 Claim, 3 Drawing Sheets

BREATH TEST FOR HELICOBACTER PYLORI

This application is a continuation of application Ser. No. 08/674,249, filed Jul. 1, 1995, now abandoned.

BACKGROUND OF THE INVENTION

1. Field of the Invention

The invention relates to a method of determining the presence of *Helicobacter pylori* infection in a human, by breath analysis.

2. Brief Description of Related Art

Gastric infection with *Helicobacter pylori* is now widely recognized as a major cause of chronic dyspepsia, gastritis, and peptic ulcer disease. Treatment of the infection with antimicrobial therapy is inexpensive and frequently curative, but diagnosis may be expensive and invasive when endoscopy and gastric biopsy are employed. This has stimulated interest in breath tests for the non-invasive diagnosis of gastric infection with *H. pylori*. The urea breath test is based upon the observation that *H. pylori* possesses an enzyme, urease, which is not present in mammals. In an infected patient, an oral dose of urea is broken down in the stomach by bacterial urease to form ammonia and carbon dioxide. If the urea is radiolabelled with an isotope of carbon ($^{13}C$ or $^{14}C$), the appearance of isotopically labelled $CO_2$ in the breath provides a clinically useful diagnostic marker of infection with *H. pylori*; see Alper J.: Ulcers as an infectious disease. Science 1993;260: 159–160;

Phillips M.: Breath tests in medicine. Scientific American 1992; 267(1): 74–79;

Stubbs J. B. and Marshall B. J.: Radiation dose estimates for the carbon-14-labelled urea breath test, J Nucl Med 1993;34:821–825.

A number of clinical studies with the $^{14}C$-urea breath test have been reported; see Marshall B. J., Plankey M. W., Hoffman S. R. et al: A 20-minute breath test for *Helicobacter pylori*, Amer J Gastroenterol 199 1;86:438–445;

Novis B. H., Gabay G., Leichmann G. et al: Two point analysis 15-minute $^{15}C$-urea breath test for diagnosing *Helicobacter pylori* infection, Digestion 1991;50:16–21;

Debongnie J. C., Pauwels S., Raat A. et al: Quantification of *Helicobacter pylori* infection in gastritis and ulcer disease using a simple and rapid carbon-14-urea breath test, J Nucl Med 1991;32:1192–1198;

Moshkowitz M., Baratz M., Tiomny E. et al: $^{14}C$-urea breath test—a simple, noninvasive method for the detection of *Helicobacter pylori* infections, Isr J Med Sci 1993;29:94–97;

Kao C. H., Huang C. K., Wang S. J. et al: Accuracy of a rapid 10-minute carbon-14 urea breath test for the diagnosis of *Helicobacter pylori*-associated peptic ulcer disease, Eur J Nucl Med 1993;20:708–711;

Glupczynski Y., Bourdeaux L., Verhas M. et al: Use of a urea breath test versus invasive methods to determine the prevalence of *Helicobacter pylori* in Zaire. Eur J Clin Microbiol Infect Dis 1992; 11:322–327;

Morales E. O. S., Vorackova F. V., Perez J. deJ V., Alonso S. S., Angeles A. A., River J. E. and Reynoso S. G.: (Optimization of the 14-C urea breath test for the detection of *H. pylori* in dyspeptic patients), La Revista de Investigacion Clinica 1995;47:109–16.

Although these reports originated from several different geographical sources (Asia, Africa, Europe, Latin America, the Middle East and the United States), they were all similar in the techniques employed and in their clinical findings. The method of Marshall et al., supra., is typical: patients ingested a dose of 5 microcuries of $^{14}C$-urea in 20 ml water, then expired through a $CO_2$ trap containing methanol, hyamine and a pH indicator. Breath collection ceased when the solution became colorless. The trap, which had captured approximately 1.0 mmol $CO_2$, was assayed for $^{14}CO_2$ in a liquid scintillation counter. Results were virtually identical to those reported in the other studies mentioned above: there were no false-positives (i.e. the specificity was 100%) but there was a low incidence of false-negatives (i.e. the sensitivity was less than 100%).

Existing $^{14}$-C-urea breath tests are elegant in conception but may be difficult to use in clinical practice. The major problems arise from the breath collection methods. Patients are required to blow through a tube into a water trap containing a reagent which captures the radiolabelled $CO_2$. This technique is open to several criticisms:

(1) It is time consuming, requiring a minute or longer to collect a sample;

(2) It may be uncomfortable for the patient, especially the elderly and those with respiratory diseases;

(3) It is potentially hazardous, in that a poorly coordinated patient who sucks instead of blowing may ingest a mouthful of toxic reagents;

(4) It inaccurately measures the volume of collected breath, since the end point (a color change in the reagent) is subjective and difficult to identify;

(5) It is inconvenient, since it requires the use of liquids which may easily be spilled;

(6) It yields a sample contaminated with dead-space air, whereas the radiolabelled $CO_2$ is only present in the alveolar breath; and (7) It requires that the patient expire against resistance, which could result in a potentially hazardous Valsalva maneuver in the elderly or debilitated.

In response to these deficiencies in existing methods, we have developed an improved version of the known $^{14}C$-urea breath test which requires that the patient blow into a bag rather than a liquid trap. In addition, we sought to optimize this test by varying (a) the time of collection of the breath sample after administration of the dose of $^{14}C$-urea, and (b) the concentration of potassium hydroxide employed in the liquid trap for the capture of the radiolabelled $CO_2$.

SUMMARY OF THE INVENTION

The invention comprises a process for determining the presence of *H. Pylori* infection in a mammal, including a human suffering from said infection, which comprises;

administering systemically to the human a detectable dose of radiolabelled urea;

collecting a representative sample of breath expired by the mammal;

separating from the collected breath any radiolabelled carbon dioxide present, in potassium hydroxide solution; and analyzing the solution to determine if radiolabelled carbon dioxide is present as an indication that said human suffers the infection.

This breath test provides a safe, convenient and highly sensitive and specific diagnostic test for gastric infection with *H. pylori*. It is technically uncomplicated to perform and patients find it highly acceptable. The test is well-suited to rapid diagnostic testing in ambulatory patients who require screening for the etiology of their dyspepsia, or follow-up after treatment of *H. pylori* infection with antibiotics; see Atherton J. C. and Spiller R. C.: The urea breath test for *Helicobacter pylori*. Gut 1994;35:723–725.

DETAILED DESCRIPTION OF THE PREFERRED EMBODIMENTS OF THE INVENTION

Figure 1:
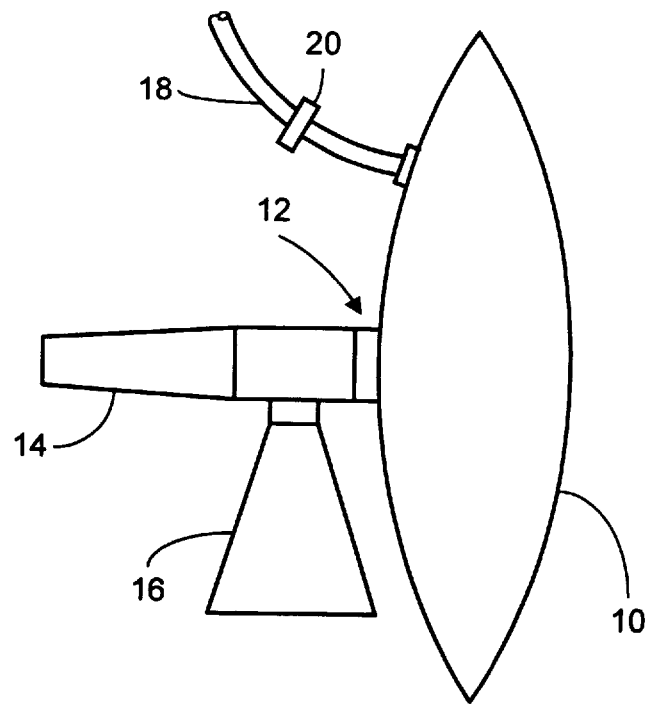
FIG. 1 is a schematic diagram showing apparatus used for breath collection in the process of the invention.
Figure 2:
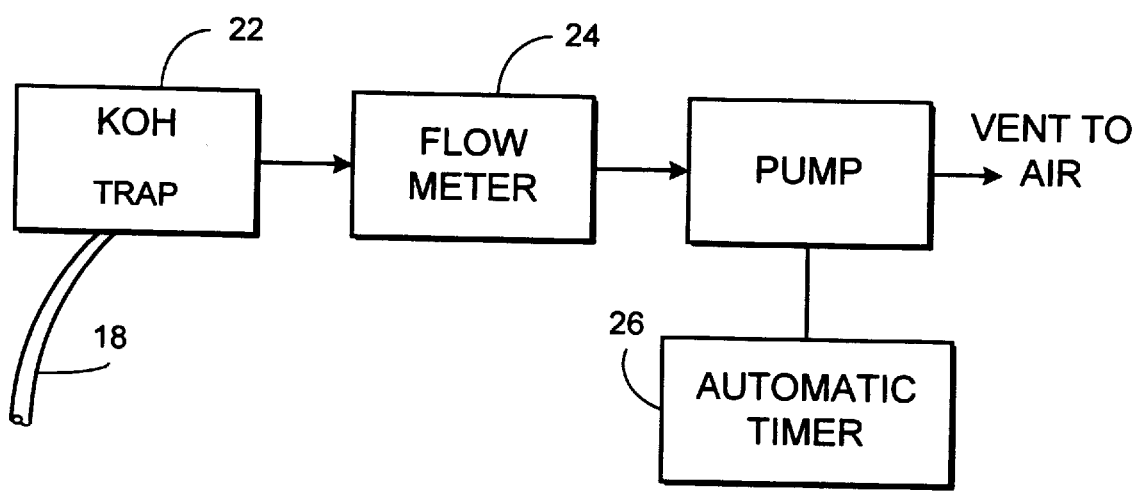
FIG. 2 shows that alveolar breath samples are pumped from the bag 10 (of FIG. 1) through the potassium hydroxide trap, where the $^{14}CO_2$ is captured.

With reference to the accompanying drawing of FIG. 1, a schematic drawing showing apparatus employed in the collection of breath from a patient, there is seen a breath collection bag 10. These were 2.0 L bags sealed with an inlet flap valve 12; the disposable mouthpiece 14 vented to a side-bag 16 (volume 500 ml) which shunted off the dead space breath so that only alveolar breath entered the bag 10. The bag 10 was provided by Quintron Instruments Company Inc, Menomonee Falls, Wis.). As shown in FIG. 2, breath from the collecting bag 10 was carried by sampling tube 18 controlled by pressure clamp 20 bubbled through a KOH trap (a scintillation vial containing 6.0 ml KOH solution) in order to capture the $CO_2$. A flow meter 24 was adjusted to a rate of 250 ml/min and automatic timer 26 for 6.0 min, so that a sample of 1500 ml alveolar breath was assayed. 14 ml Ecoscint A, an environmentally safe scintillation fluid (National Diagnostics, Atlanta, Ga.) was added. Another scintillant (Dimiscint, National Diagnostics, Atlanta, Ga.) yielded consistently similar diagnostic results with the added advantage that the test could be read within 15 minutes of performing $CO_2$ capture. The trap contained 8.0 mM KOH during the pilot phase; during the optimization phase, traps containing 8.0 mM, 80.0 mM, 800 mM and 8000.0 mM KOH were employed. The sample was read in a liquid scintillation counter for 1.0 min using the pre-set carbon-14 window without quench correction (Pilot phase: LKB 1217 Rackbeta, Wallac Inc, Gaithersburg, Md.; optimization phase: Beckman LS 3801, Beckman Instruments, Somerset, N.J.). Samples were kept in the dark and read 24 hr after the time of capture of the $CO_2$ sample in order to minimize the effects of chemiluminescence and photoluminescence.

The following examples and preparations describe the manner and process of making and using the invention and set forth the best mode contemplated by the inventor of carrying out the invention but are not to be construed as limiting the invention.

Preparation of unit doses $^{14}C$-urea was purchased from New England Nuclear E. I. Du Pont Research Products, Boston, Mass. (250 microcuries in 0.25 ml ethanol solution) and diluted with methanol. Unit doses containing 5.0 microcuries in 2.5 ml were prepared in individual sealed containers. Each unit dose was diluted with tap water to a volume of 20 ml prior to use.

The unit dose was administered orally to each subject prior to breath analysis.

Human Studies (a) Pilot phase: A group of 38 fasting patients was studied following gastroscopy in the endoscopy unit of St. Vincent's Medical Center of Richmond, Staten Island. All were undergoing evaluation for dyspepsia. Infection with *H. pylori* was confirmed or excluded by testing gastric biopsy specimens for urease activity (CLO test, Delta West Pty Ltd, Bentley, Western Australia). Breath tests were performed in the recovery area at least 30 min after the conclusion of the EGD when patients had recovered their gag reflexes. Breath samples were collected at zero time (before administration of the radiolabelled urea) then at 10, 20 and 30 min.

(b) Optimization phase: 53 additional patients were studied in the same fashion, except that four breath samples were collected 10 min after administration of the radiolabelled urea.

RESULTS (a) Pilot phase: The excretion of radiolabelled $CO_2$ in the breath reached a peak at 10 min with a clear separation between the infected and non-infected patients (p<0.001, 2-tailed t-test) as shown graphically in FIG. 3.

Figure 3:
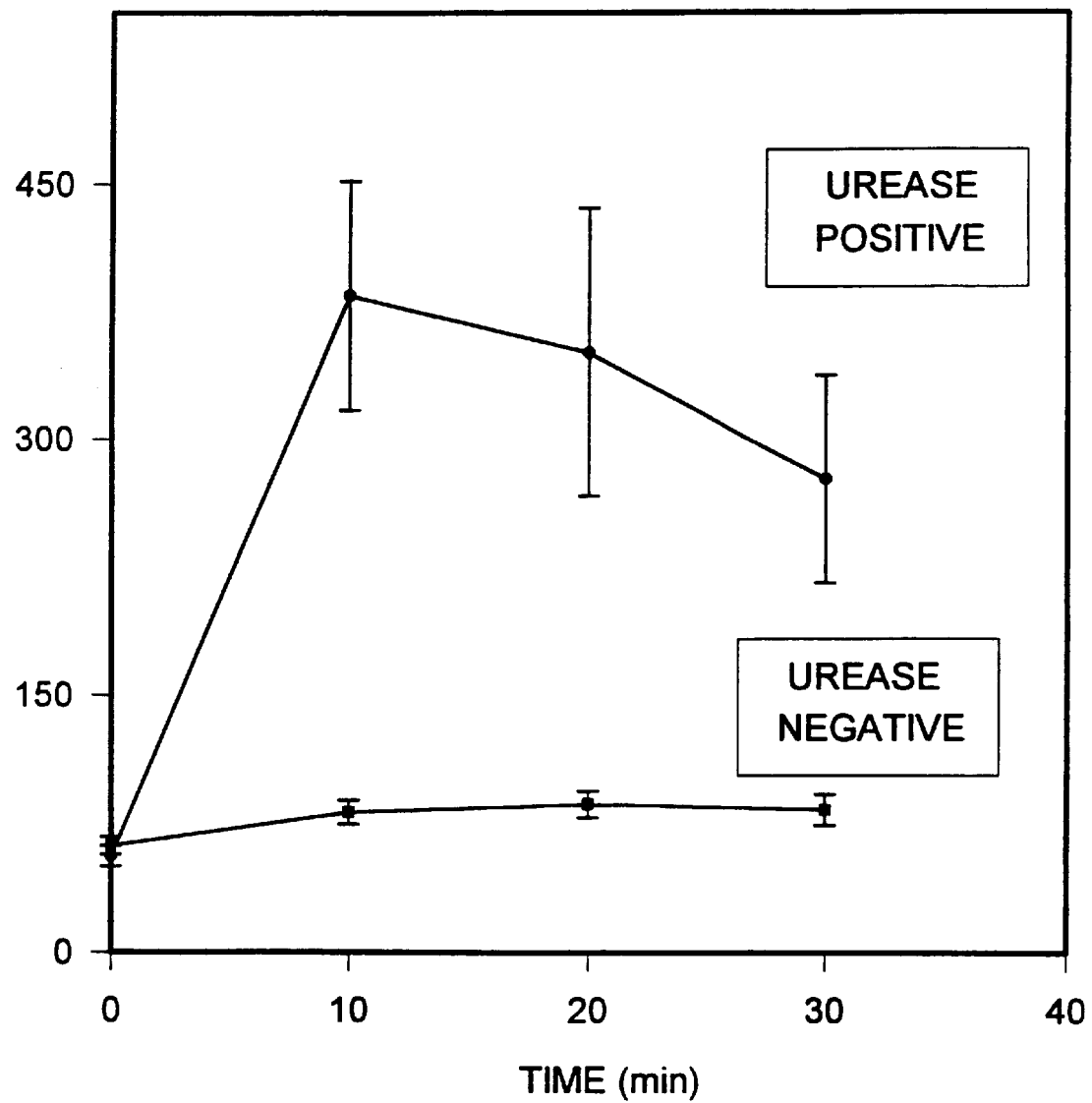
FIG. 3: Shows graphically the effects of varying the time of collection of breath sample: Mean radioactivity (bar=SD) in the breath following dosage with radiolabelled urea. 38 subjects were studied (15 infected with *H. pylori*, 23 uninfected). The difference between the two groups was greatest at 10 min after dosage (p<0.001, 2-tailed t-test).
Figure 4:
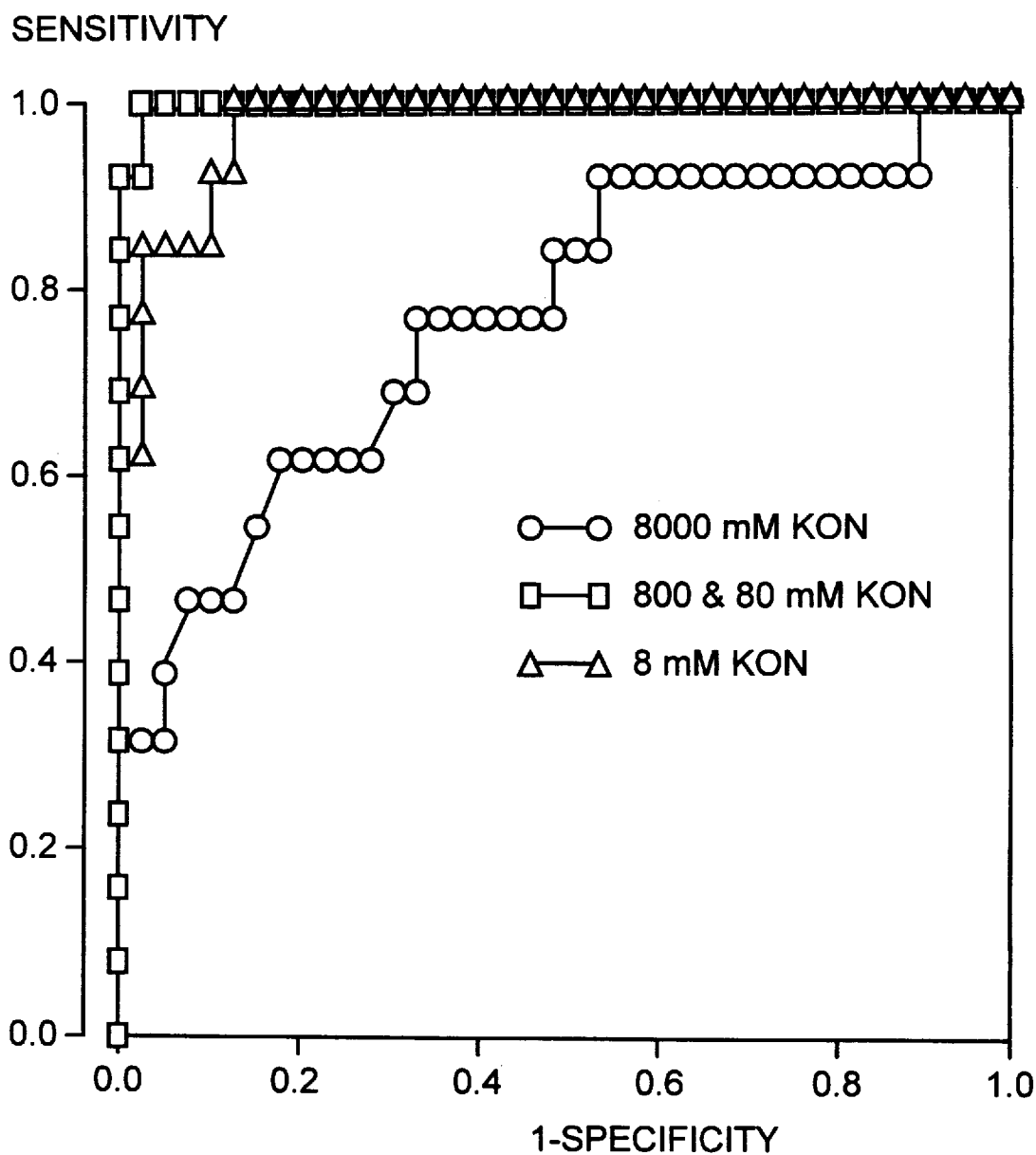
FIG. 4: Shows graphically ROC curves comparing the effects of different concentrations of KOH in a liquid trap). Concentrations of 80 and 800 mM KOH yielded identical ROC curves and provided the best combination of sensitivity and specificity.

(b) Optimization phase: ROC curves comparing the results obtained with different concentrations of KOH are shown in FIG. 3.

No patients reported discomfort in donating breath specimens or any adverse effects of the test in either phase of the study. Diagnostic findings at gastroscopy for all patients are shown in Table 1, below.

TABLE 1

| Endoscopy findings in patients | | | | |
|---|---|---|---|---|
| | UREASE TEST RESULTS | | | |
| | PILOT PHASE | | OPTIMIZATION PHASE | |
| | POSITIVE | NEGATIVE | POSITIVE | NEGATIVE |
| Gastric ulcer (GU) | 2 | 1 | 1 | 2 |
| Duodenal ulcer (DU) | 1 | 0 | 1 | 2 |
| GU and DU | 1 | 0 | 0 | 0 |
| Gastro-duodenitis | 10 | 18 | 2 | 5 |
| Peptic ulcer (site unspecified) | 0 | 0 | 1 | 9 |
| Other | 1 | 4 | 5 | 17 |
| Results unavailable | 0 | 0 | 3 | 5 |
| Total | 15 | 23 | 13 | 40 |

The use of vented bags for the collection of breath averted all of the disadvantages of liquid-trap collection methods, and provided some important advantages:

(1) Uncontaminated sample: The sample in the breath-collecting bag contained alveolar breath only; the dead-space breath was shunted to the side bag and did not dilute the sample which was analyzed.

(2) Patient acceptability: Patients were generally able to fill the bag with a single expiration, though two or more breaths were occasionally required in the elderly or those with respiratory disease. The system offered close to zero resistance to expiration, thereby reducing the risk of a Valsalva maneuver in the elderly or debilitated.

(3) Liquid-free collection system: Patients were not required to blow through a liquid trap, such as those described in previous reports of the carbon-14 urea breath test. The dangers of accidental ingestion or spillage were thereby eliminated.

This study also demonstrated benefits arising from optimization of two other variables: the time of collection of the breath sample and the concentration of KOH in the liquid trap. The concentration of $^{14}CO_2$ in the breath reached a peak value at 10 min following dosage of the $^{14}C$-urea. The ROC curves displaying the best combination of sensitivity and specificity of the test were observed with 80 and 800 mM KOH.

Some interaction between the KOH solution and the scintillation fluid was observed: precipitation sufficient to cause two-phase separation occurred in the vials containing 8000 mM KOH; some precipitation was observed with 800 mM KOH and none with 8 mM and 80 mM KOH. Also, the interaction between KOH and scintillant was found to cause chemiluminescence which was initially sufficient to cause erroneous readings; however this abated to undetectable levels when Dimiscint was employed instead of Ecoscint A.

Only one false-positive result prevented the breath test from achieving 100% sensitivity and 100% specificity when KOH concentrations of 80 mM and 800 mM were employed.

There are advantages and disadvantages to using urea labelled with either $^{13}C$ or $^{14}C$. $^{13}C$-urea is a stable isotope which is safe for human consumption; on the other hand, detection of $^{13}CO_2$ requires specialized and expensive mass-spectroscopic equipment which is not generally available, though this may change with the advent of newer assays.

$^{14}C$-urea yields $^{14}CO_2$ which can be detected in a liquid scintillation counter, an instrument which is widely available and considerably less expensive than a mass-spectrometer; on the other hand the compound is a weak beta-emitter and exposes tissues to radiation. However, Stubbs and Marshall, supra., have determined that the dose of radiation exposure from a single $^{14}C$-urea breath test exposes an average individual to approximately 1/800 of the radiation encountered from natural sources during the course of a year. This low dosage of radiation combined with the comparatively low cost of radiolabelled urea and liquid scintillation counters has led to widespread acceptance of the safety of the $^{14}C$-urea breath test in several countries outside the United States.

What is claimed is:

1. A process for determining the presence of *H. pylori* infection in the gastrointestinal tract of a mammal, including a human suffering from said infection, which comprises;

administering systemically to the human a detectable dose of radiolabelled urea;

collecting in a liquid-free bag a representative sample of alveolar breath only, expired by the mammal within 10 to 30 minutes after administering the radiolabelled urea;

separating from the collected breath any radiolabelled carbon dioxide present, in 80 to 800 mM concentration potassium hydroxide solution; and analyzing the solution to determine if radiolabelled carbon dioxide is present as an indication that said human suffers the infection.

* * * * *